(12) United States Patent
Orlewski et al.

(10) Patent No.: US 7,643,145 B2
(45) Date of Patent: Jan. 5, 2010

(54) DETECTION AND ANALYSIS OF OPTICAL SENSING PROBES

(75) Inventors: Pierre Orlewski, Etterlbruck (LU); Laurent Federspiel, Munsbach (LU)

(73) Assignee: IEE International Electronics & Engineering S.A., Luxembourg (LU)

( * ) Notice: Subject to any disclaimer, the term of this patent is extended or adjusted under 35 U.S.C. 154(b) by 250 days.

(21) Appl. No.: 11/658,939

(22) PCT Filed: Jul. 27, 2005

(86) PCT No.: PCT/EP2005/053669

§ 371 (c)(1), (2), (4) Date: Jan. 29, 2007

(87) PCT Pub. No.: WO2006/010768

PCT Pub. Date: Feb. 2, 2006

(65) Prior Publication Data

US 2007/0247627 A1  Oct. 25, 2007

(30) Foreign Application Priority Data

Jul. 28, 2004  (LU) .................................. 91092

(51) Int. Cl.
*G01N 21/00* (2006.01)
(52) U.S. Cl. ...................... 356/437; 356/442
(58) Field of Classification Search ............ 356/437, 356/442; 257/202, 204
See application file for complete search history.

(56) References Cited

U.S. PATENT DOCUMENTS

| | | | |
|---|---|---|---|
| 5,376,336 A | 12/1994 | Luebbers et al. | |
| 6,537,829 B1 | 3/2003 | Zarling et al. | |
| 6,909,126 B1 * | 6/2005 | Janesick | 257/184 |
| 7,064,311 B2 * | 6/2006 | Jung et al. | 250/205 |
| 7,557,335 B2 * | 7/2009 | Hong et al. | 250/214.1 |
| 2002/0139918 A1 * | 10/2002 | Jung et al. | 250/205 |
| 2003/0062549 A1 * | 4/2003 | Lauxtermann et al. | 257/204 |
| 2003/0068827 A1 | 4/2003 | Morris et al. | |
| 2004/0129861 A1 * | 7/2004 | Jung et al. | 250/208.1 |
| 2007/0265513 A1 * | 11/2007 | Schenkman et al. | 600/363 |
| 2008/0200780 A1 * | 8/2008 | Schenkman et al. | 600/310 |

FOREIGN PATENT DOCUMENTS

WO  WO 99/18434  4/1999

OTHER PUBLICATIONS

International Search Report; PCT/EP2005/053669; Nov. 23, 2005.

* cited by examiner

*Primary Examiner*—Roy Punnoose
(74) *Attorney, Agent, or Firm*—Cantor Colburn LLP

(57) ABSTRACT

The present invention relates to the detection of optical sensors by means of measurement of information relative to the signal intensity and signal modulation phase shift. The proposed method employs the use of CMOS and/or CCD imager and illuminations with different wavelengths. The system is able realize a contactless measurement of a phase shift to curse on a gas concentration an distance.

14 Claims, 3 Drawing Sheets

CMOS based shutter structure

DETECTION AND ANALYSIS OF OPTICAL SENSING PROBES

BACKGROUND OF THE INVENTION

The present invention relates to the detection of optical sensors by means of measurement of information relative to a signal intensity and a signal modulation phase shift.

The market of inexpensive, smart and disposable intelligent labels, RFID and smart tags is rapidly growing. The most demanding properties to be sensed by such devices are temperature, pressure, moisture, pH, gas concentrations ($CO_2$, CO, $NH_4$, $O_2$, and others) and the concentration of specific chemical ions (ammonia, etc). The basic challenge today consists in bringing on the market a smart solution both on the sensor as on detecting device side. In a most general approach, the sensing element needs to be included into the detection area in such a way that is able to sense the interesting propriety (gas, pH, . . . ) while still able to be remotely activated and interrogated by the distant measurement unit.

One of the future customers of such technology is the packaging industry, where several goods, depending to their nature, need to be packaged under well defined and controlled conditions. Thus, chemical, pharmaceutical and electronic industries are frequently confronted to the problem of exposure to factors like temperature, oxygen or moisture, which excess is leading to the premature degradation of packaged good. The food packaging industry is typically struggling with too high concentration of oxygen and to high temperature.

There are several other applications, where remote, optical evaluation of carbon monoxide, dioxide, ammonia or specific chemical ions is necessary for the general safety or product shelf life reasons. A good example of today's industrial needs is the oxygen sensing for food packaging industry that is currently employing MAP (Modified Atmosphere Packaging) packaging foils to guarantee a constant and low oxygen concentration to the packaged goods. Here, the solution will consist on placing inside such package, or placing it directly on the packaging foil, an oxygen-sensitive element able measure the $O_2$ concentration and communicate this information optically or by RF to the detector unit.

Very strong price pressure, small size requirement and real need of disposable sensors eliminate a variety of "smart tags" communicating remotely with detection or analyzing unit by RF.

The solution of choice in this case consist on disposing inside the package of chemical compound whose light emission properties are directly depending to the oxygen concentration. This can be easily achieved if using one of several possible easily, optically excitable organometallic complexes (transition metal-organic complexes, preferably highly aromatic compounds like porphyrins, etc., for which the oxygen particles are fluorescence quenchers. Thus, the sensing compound or luminescence probe, after its prior excitation by a remote illumination at a specific wavelength, will emit an optical signal (fluorescence) which decay in time is directly informing of temperature and of oxygen concentration. This quencher (here: $O_2$) to signal decay relation is described by the Stern-Volmer relation.

The measurement can relay on the emitted light intensity or on the emission (fluorescence) life time. In the first case, the dependency to the luminescence probe concentration and its purity constitutes a strong disadvantage. The measurement based on fluorescent signal decay, fluorescent modulation phase shift or polarization type and change of emitted light are all not depending to this. Unfortunately, a fluorescence intensity and life time of almost all interesting compounds is not only depending to the concentration of specific fluorescence quenchers but also to temperature.

There is however, a possibility to use another, optically activated compound, the fluorescence intensity or decay time of which is only depending on the temperature. Such compound, just employed as standalone, gives an excellent solution for the disposable and remote temperature sensor, while used along with a quencher-dependent compound, offers internal temperature calibration of the Stern-Volmer relationship linking the quencher concentration, temperature and fluorescence decay. Oregon Green-488 fluorescent dye can be employed for this purpose along with one of several known oxygen-sensitive compounds like Ru(II)[dpp(SO3Na)2]3) Cl2, Ru(II)(dpp), PdTCPPP, PtOEP or other Cr, Mn, or transition metals-organic complexes. An important characteristic of using fluorescence probes is that they are reversible within a very short time period to encompass rapid temperature or atmosphere changes.

Current technology of excitation/analyzing units employs lock-in analyzers, modulated signal generators and photomultipliers. These devices are very complex and have a very large size. Downsizing of such equipment to handheld devices required in several applications is not possible both from a technical and a commercial (high prize) point of view.

BRIEF DESCRIPTION OF THE DRAWINGS

The present invention will be discussed with reference to the attached drawings, wherein.

BRIEF SUMMARY OF THE INVENTION

Figure 1:
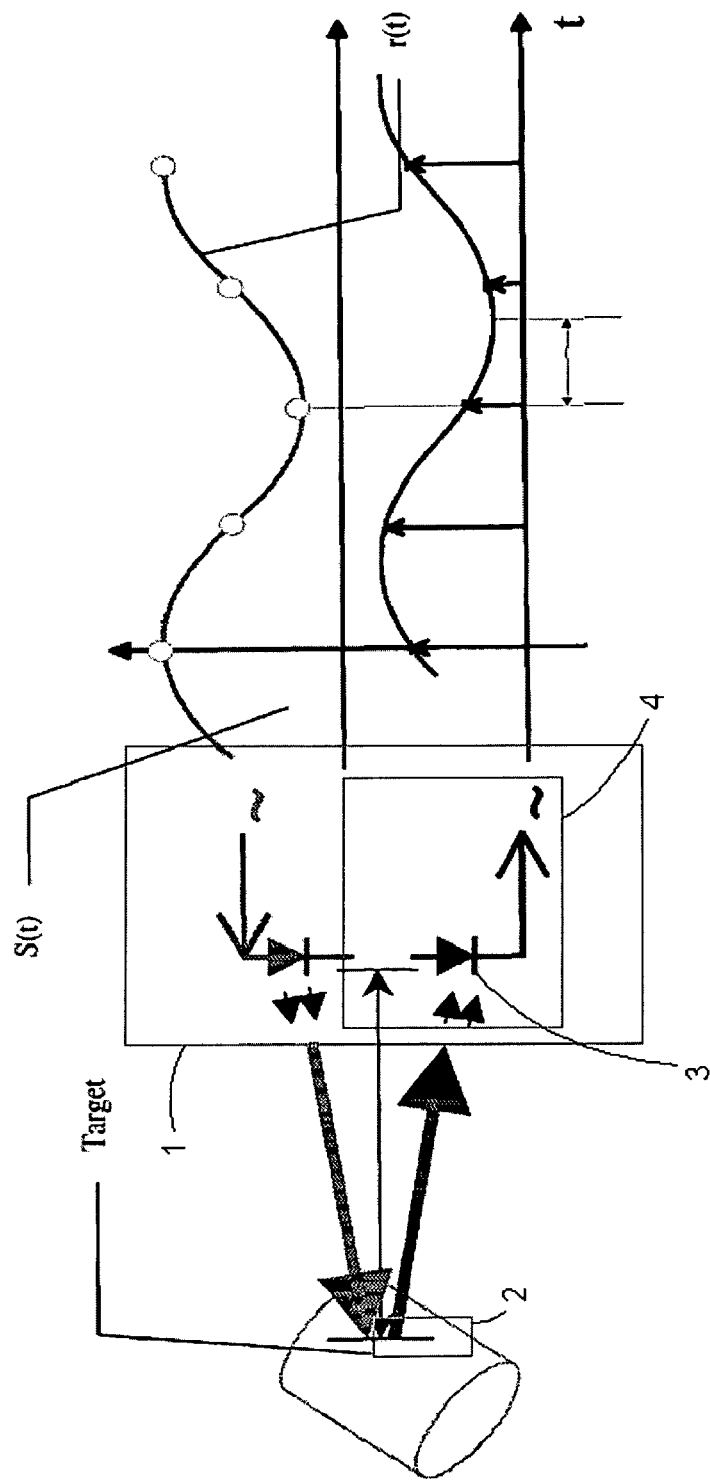
FIG. 1 schematically illustrates the principle of the optical measurement.
Figure 2:
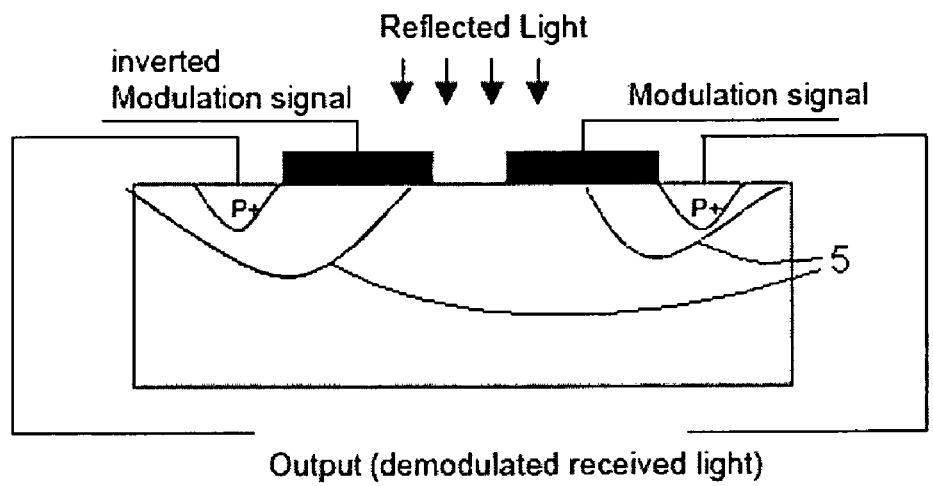
FIG. 2 schematically represents the implementation of an electronic shutter as an optical lock-in pixel structure in CMOS imager sensors.
Figure 3:
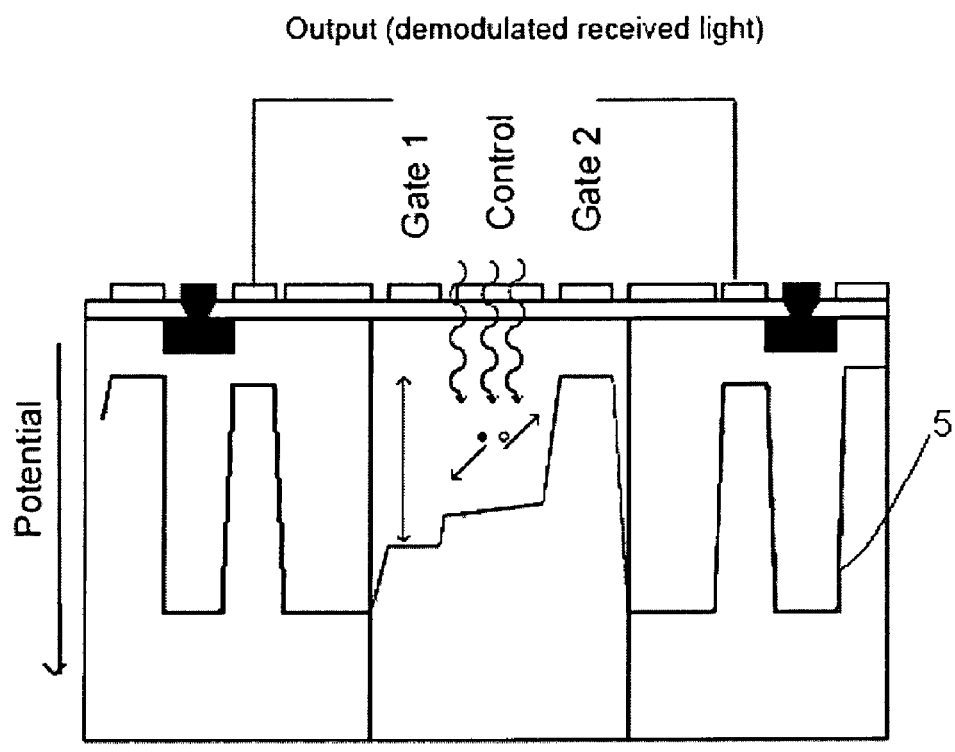
FIG. 3 schematically represents the implementation of an electronic shutter as an optical lock-in pixel structure in CCD imager sensors.

In order to overcome the abovementioned problems, the present invention proposes a device for the interrogation 1 of an optical sensing probe 2, comprising a detecting unit for detecting an optical wave emitted from said optical sensing probe 2. According to the invention, the said detecting unit comprises at least one CMOS and/or CCD imager 3 or at least one CMOS and/or CCD sensor matrix 4.

The detection device preferably comprises at least one shutter element associated to said imager or sensor matrix, said at least one shutter element for demodulating an optical wave emitted from said optical sensing probe. This shutter element may comprise a mechanical shutter or an electrical shutter 5 implemented in a silicon structure of the CMOS or CCD sensor (lock-in pixel structure).

In a preferred embodiment, the device further comprises an illumination source of a wavelength corresponding to an absorption wave-length of said optical sensing probe. Alternatively the device may comprise multiple illumination sources of different wavelengths, said wavelengths corresponding to an absorption wavelength of different optical sensing probes.

The present invention accordingly proposes a handheld and relatively inexpensive device, which is obtained when using optical sensor technology along with illumination (LED) source of the wavelength corresponding to absorption of optical sensing compound (in case of RuIIDPP and similar complexes, as well as in case of Oregon Green-488 dye, absorption band is situated around 420 nm). The CMOS sensor matrix must cover the emission bandwidth, which in case of the cited compounds is located between 500 and 750 nm. Both the signal intensity and the signal modulation phase shift need to be measured to make the detecting electronics really versatile and multipurpose.

The realization of the measurement device is based on an optical matrix sensor, which is able to demodulate the reflected modulated light in such a way that the phase shift can be extracted. The sensing part has to be realized with an electronic shutter or a mechanical shutter to split the modulation. The basic of the measurement is well known due to the principle of the time of flight (TOF) measurement using a phase shift measurement as described in T. Spirig et al., "The multitap lock-in CCD with offset subtraction", *IEEE Transactions on electron devices*, Vol. 44, No. 10, 1643-1647, October 1997 or R. Lange, P. Seitz, "Solid State Time-Of-Flight Range Camera", IEEE Journal of Quantum Electronics, 37 (2001) 390.

The difference between the use of the technology for the distance measurement is that the measurement has to be done in a special range of wavelengths.

The device according to the present invention may be used in a number of different applications such as for the detection of gas concentrations in a sensing area, wherein said optical sensing probes are responsive to the gas concentrations to be determined, or for the detection of an air quality ($CO_2$ and $O_2$ concentrations, moisture and temp) in a car or inside any confined or open space. Furthermore the device can be used for remote temperature sensing, wherein said optical probe 2 comprises a temperature sensitive, luminescent dye.

DETAILED DESCRIPTION OF THE INVENTION

The sensing unit has to be configured such that the reflection of the target is measured in the follower form. If a source illumination is emitted as $S(t)=\sin(2\pi f_m t)$, the reflected light on the sensor will have a form corresponding to $r(t)=\sin(2\pi f_m t-\varnothing)$, wherein $f_m$ represents a frequency of modulation t represents a time and $\varnothing$ represents a phase shift.

The demodulation on the receiver side has the possibility to demodulate the incoming wave front r(t) depending on the emitted wave front S(t).

The realization of the so-called mixer is dependent on the used sensor structure. With a standard matrix sensor, the demodulation can e.g. be achieved by a mechanical shutter. A more efficient way to achieve the demodulation is to implement an electrical shutter in the silicon structure of the CCD sensor. In this embodiment it is possible to provide two gates on one sensitive area, which are controlled with the modulation signal. As a result the signals at the gates have the direct information for the phase shift calculation.

During an opening time of the shutter corresponding to maximally half a modulation period, each sensitive area collects two signals at its two gates, which allow calculating the phase shift.

As the phase shift is also dependent on the distance between the light source and the sensing probe and the distance between the sensing probe and the camera, this is corrected for. The pixels or sensing areas, which do not seen the sensing probe are used for the distance measurement.

On the basis of this sensor principle, the measurement system can be realized as a matrix with the possibility to observe a large field of view (FOV). To enlarge the field of application, the use of different optical filters for different types of gas can be adapted to the optical active area.

The invention claimed is:

1. Device for the interrogation of an optical sensing probe, comprising a detecting unit for detecting an optical wave emitted from said optical sensing probe, said detecting unit comprising at least one CMOS and/or CCD imager, and at least one shutter element associated to said imager, said at least one shutter element for demodulating an optical wave emitted from said optical sensing probe, said shutter element comprising an electrical shutter implemented in a silicon structure of the CMOS or CCD imager.

2. Device according to claim 1, wherein said shutter element is implemented as a lock-in pixel structure of the CMOS or CCD imager or sensor.

3. Device according to claim 1, further comprising at least one illumination source of a wavelength corresponding to an absorption wavelength of said optical sensing probe.

4. Device according to claim 1, further comprising multiple illumination sources of different wavelengths, said wavelengths corresponding to an absorption wavelength of different optical sensing probes.

5. Device according to claim 1, wherein said optical sensing probes are responsive to gas concentrations to be determined in a sensing area.

6. Device according to claim 1 further configured for the detection of an air quality in a car or inside any confined or open space.

7. Device according to claim 1, wherein said optical probe comprises a temperature sensitive, luminescent dye for remote temperature sensing.

8. Device for the interrogation of an optical sensing probe, comprising a detecting unit for detecting an optical wave emitted from said optical sensing probe, said detecting unit comprising at least one CMOS and/or CCD sensor matrix, and at least one shutter element associated to said sensor matrix, said at least one shutter element for demodulating an optical wave emitted from said optical sensing probe, said shutter element comprising an electrical shutter implemented in a silicon structure of the CMOS or CCD sensor.

9. Device according to claim 8, wherein said shutter element is implemented as a lock-in pixel structure of the CMOS or CCD imager or sensor.

10. Device according to claim 8, further comprising at least one illumination source of a wavelength corresponding to an absorption wavelength of said optical sensing probe.

11. Device according to claim 8, further comprising multiple illumination sources of different wavelengths, said wavelengths corresponding to an absorption wavelength of different optical sensing probes.

12. Device according to claim 8, wherein said optical sensing probes are responsive to the gas concentrations to be determined in a sensing area.

13. Device according to claim 8 further configured for the detection of an air quality in a car or inside any confined or open space.

14. Device according to claim 8, wherein said optical probe comprises a temperature sensitive, luminescent dye for remote temperature sensing.

* * * * *